United States Patent
Mousa

(10) Patent No.: US 11,445,917 B2
(45) Date of Patent: Sep. 20, 2022

(54) THERMOGRAPHIC DEVICE FOR MEASUREMENT OF DIFFERENTIAL TEMPERATURES IN TISSUE

(71) Applicants: WELWAZE MEDICAL INC., Miami, FL (US); Samir Mousa, Boonton, NJ (US)

(72) Inventor: Samir Mousa, Boonton, NJ (US)

(73) Assignee: Welwaze Medical Inc., Miami, FL (US)

( * ) Notice: Subject to any disclaimer, the term of this patent is extended or adjusted under 35 U.S.C. 154(b) by 356 days.

(21) Appl. No.: 16/214,928

(22) Filed: Dec. 10, 2018

(65) Prior Publication Data

US 2019/0209019 A1    Jul. 11, 2019

Related U.S. Application Data

(60) Provisional application No. 62/596,223, filed on Dec. 8, 2017.

(51) Int. Cl.
*A61B 5/01* (2006.01)
*A61B 5/00* (2006.01)
*A61B 10/00* (2006.01)

(52) U.S. Cl.
CPC ........... *A61B 5/015* (2013.01); *A61B 5/01* (2013.01); *A61B 5/4312* (2013.01); *A61B 10/0041* (2013.01); *A61B 2562/0276* (2013.01); *A61B 2562/046* (2013.01)

(58) Field of Classification Search
CPC ......... A61B 5/015; A61B 5/01; A61B 5/4312; A61B 2562/046; A61B 2562/0276; A61B 10/0041
See application file for complete search history.

(56) References Cited

U.S. PATENT DOCUMENTS

| | | | |
|---|---|---|---|
| 2,490,933 A | * | 12/1949 | Tornquist ............... G01K 11/06 116/219 |
| 3,830,224 A | | 8/1974 | Vanzetti et al. |
| 3,847,139 A | | 11/1974 | Flam |
| 4,101,696 A | | 7/1978 | Jennen |
| 4,186,731 A | | 2/1980 | Clark |
| 4,190,058 A | | 2/1980 | Sagi |
| 4,232,552 A | | 11/1980 | Hof et al. |
| 4,362,645 A | | 12/1982 | Hof et al. |

(Continued)

OTHER PUBLICATIONS

New Perspectives in Breast Imaging, Chapter 5—Advances in Breast Thermography—Siva Teja Kakileti et al.
Mathematical and Computer Modelling (2011) Tumor Location and Parameter estimation by thermography, J.P. Agnelli et al.
International Journal of Heat and Mass Transfer (2017)—Infrared imaging technology for breast cancer detection—current status, protocols and new directions—Satish G. Kandlikar et al.

(Continued)

*Primary Examiner* — Rene T Towa
(74) *Attorney, Agent, or Firm* — Burns & Levinson LLP; Bruce D. Jobse; Shawn P. Foley

(57) ABSTRACT

A thermographic sensing device for measuring temperatures at one or more regions of the human body, particularly the breast, utilizes a thermographic composition deposited into linear arrays of recesses formed in the lobes of a conformable medium which is disposable against the skin. The thermographic composition includes a binary solvent system and at least one colorant, wherein the compositions in each array are formulated to melt at precise temperatures, within a diagnostically temperature relevant range, to change from a first visible color to a second visible color.

19 Claims, 6 Drawing Sheets

(56) References Cited

U.S. PATENT DOCUMENTS

| | | | |
|---|---|---|---|
| 4,397,570 A | | 8/1983 | Hof et al. |
| 4,437,471 A | | 3/1984 | Nelson |
| 4,524,778 A | | 6/1985 | Brown, Jr. et al. |
| 4,624,264 A | | 11/1986 | Sagi |
| 4,651,749 A | * | 3/1987 | Sagi ............... A61B 5/015 600/549 |
| 4,788,984 A | * | 12/1988 | Marsik ........... A61B 10/0012 436/65 |
| 5,094,545 A | | 3/1992 | Larsson et al. |
| 5,621,028 A | * | 4/1997 | Lichtenstein ........ C08K 5/0041 524/359 |
| 5,816,707 A | | 10/1998 | Hof |
| 6,077,228 A | | 6/2000 | Schonberger |
| 6,086,247 A | * | 7/2000 | von Hollen ........... A61B 5/015 374/137 |
| 6,135,968 A | | 10/2000 | Broinstein |
| 6,241,385 B1 | | 6/2001 | Hof |
| 6,419,636 B1 | | 7/2002 | Young et al. |
| 6,420,184 B1 | | 7/2002 | Hof |
| 8,574,457 B2 | | 11/2013 | Stpien et al. |
| 2014/0032819 A1 | | 10/2014 | Hyde et al. |
| 2017/0007170 A1 | * | 1/2017 | Smith .................. A61B 5/411 |

OTHER PUBLICATIONS

Thermal analysis of cancerous breast model—NIH-PA Author Manuscript—PMC Oct. 16, 2014—Arjun Chanmugam et al.
The Effect of Thermography on Breast Cancer Detection—Systematic Reviews in Pharmacy, vol. 9, Issue 1, Jan.-Dec. 2018—PR Pavithra et al.
International Seminars in Surgical Oncology—The potential role of dynamic thermal analysis in breast cancer detection—M. Salhab et al. Apr. 3, 2006.
Basnec, et al., "Relation between colour- and phase changes of a leuco dye-based thermochromic composite," Scientific Reports, (2018) 8:5511, DOI: 10.1038/s41598-018-23789-2, www.nature.com/scientificreports.
Maclaren, et al., "Design rules for reversible thermochromic mixtures," Journal of Materials Science 40 (2005) pp. 369-676.
Panak, et al., "The relation between colour and structural changes in thermochromic systems comprising crystal violet lactone, Gisphenol A, and tetradecanol," Science Direct Dyes and Pigments, vol. 136, Jan. 2017, pp. 382-289.
Extended European Search Report for EP Application No. 18886738.6, dated Mar. 24, 2022 (6 pages).

* cited by examiner

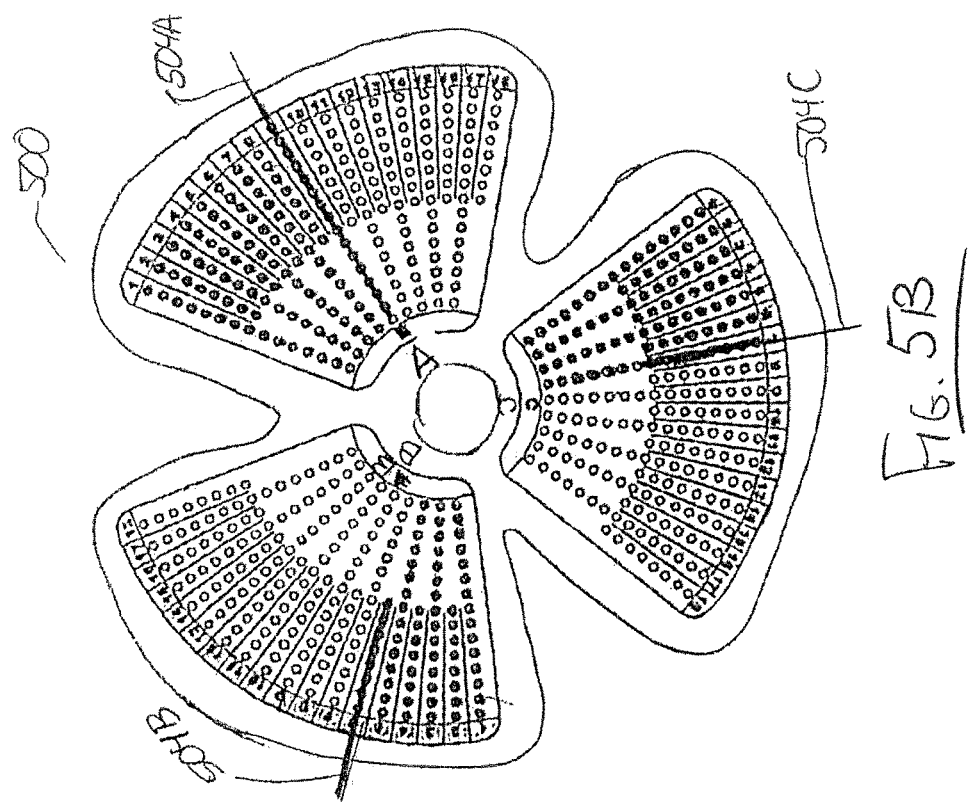
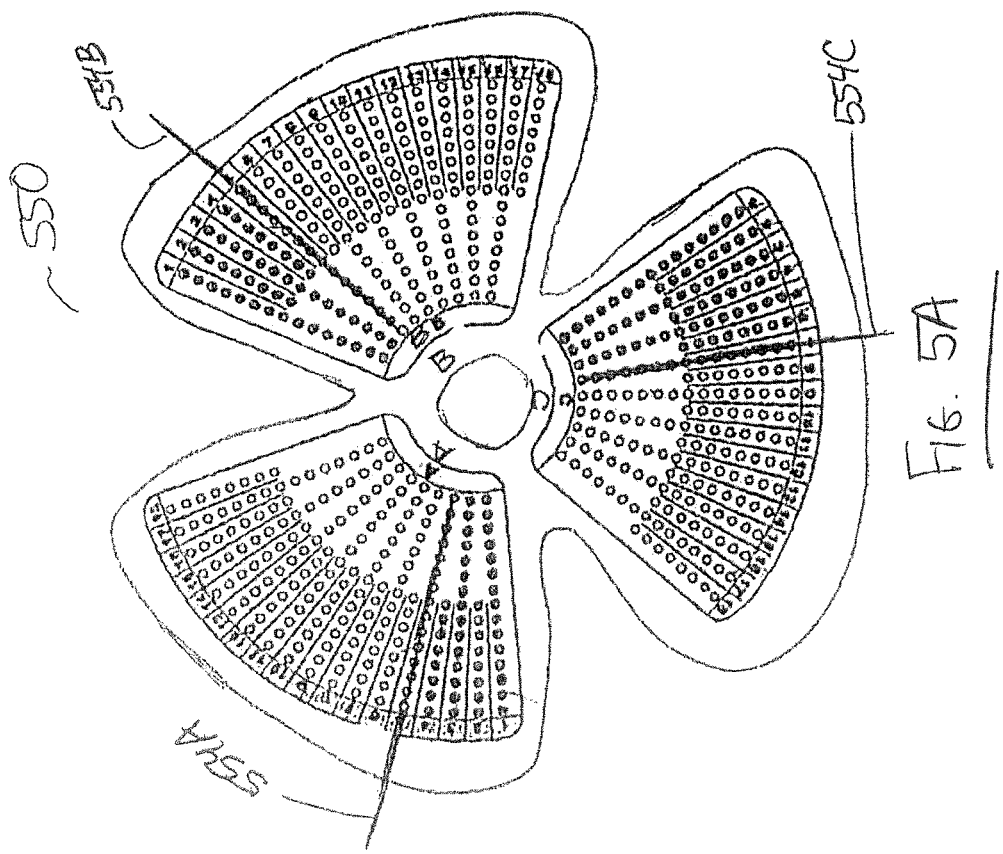

THERMOGRAPHIC DEVICE FOR MEASUREMENT OF DIFFERENTIAL TEMPERATURES IN TISSUE

BACKGROUND OF THE INVENTION

Breast cancer is the most common cancer in women worldwide and is the leading cause of cancer related deaths in developing countries, with nearly 1.7 million new cases diagnosed in 2012. Breast cancer represents 25.2% of all female cancers and is the leading cause of cancer mortality in women (14.7% of all female cancer deaths) [*International Agency for Cancer Research. World Cancer Report* 2014]. In 2017, 40,610 people (men and women) are projected to die of breast cancer in the United States. American Cancer Society "*Breast Cancer Facts & Figures* 2017-2018."

Developed countries, such as the U.S. and France, have higher incidence rates compared with the developing world. The number of new cases of breast cancer per year in the U.S. and EU amount to half of total global incidence. However, mortality rates show a different story. Breast cancer patients in the U.S. and EU usually have better access to screening and treatment and therefore have a higher survival rate. The current approach to this disease, at least in the U.S., involves early detection and treatment; it yields an 85% 10-year survival rate. Nover, et al., Int. J. Biomed. Imag. 2009; 2009:902326. Survival is directly related to stage at diagnosis, as can be seen by a 98% 10-year survival rate for patients with stages 0 and I disease compared with a 65% 10-year survival rate for patients with stage III disease. Nover, supra. The mortality rates in the developing world as a percentage of incidence is much higher, and usually due to lack of access to screening and treatment. Future incidence rates for the developing world are likely to grow, and it is estimated that by the year 2020, 70% of all new global breast cancer cases will occur in the developing world. Time Magazine, "The Changing Face of Breast Cancer," Oct. 15, 2007.

Due to the asymptomatic nature of breast cancer, tumors may be detected at any point along the diagnosis path, which begins with early detection methods such as breast self-examination (BSE) and clinical breast examination (CBE). In BSEs and CBEs, either the patient or the doctor feels the breasts looking for abnormalities or changes. It is difficult to detect small tumors with BSE and CBE. Tumors must be palpable for BSEs and CBEs to be effective. On average, when breast lumps are discovered through BSE or CBE, women will have had the disease for 10 years. Moreover, a majority of women do not know how to conduct a proper BSE. Likewise, a proper CBE takes 6-12 minutes; however, many physicians spend less than 5 minutes. Other detection methods include mammography, MRIs and ultrasounds.

Mammography has been regarded as the gold standard in breast cancer screening and detection. Since the 1980s, mammography has been the only screening method which has been proven to reduce mortality rates from breast cancer in the general population. In the general population, its sensitivity is 68%-88%. Smith et al., Radiol. Management 26(4):16-24 (2004). Almost all breast exams performed in the U.S. will use mammography before any other breast cancer detection tool. X-rays provide a visualization of the internal breast structure either on traditional film or digital scans. Depending on various factors including age, breast density, and the ability of a radiologist to interpret images, mammography can detect between 68-88% of breast cancers. Smith et al., supra. MRIs use magnetic fields to produce a cross-sectional image of the breast. Contrast material is injected into a vein creating images more detailed than those produced by mammography. Ultrasound uses high frequency sound waves to detect abnormal concentrations of cells in the breast. If results are positive, all detection methods lead to a biopsy procedure to diagnose breast cancer. A biopsy involves removing a sample of tissue through a needle for analysis. Currently, biopsy is the only definitive way to establish the presence of cancer cells and diagnose breast cancer.

These methods are not without disadvantages. Mammography has several drawbacks, including the pain associated with compression of the breast during the scan, and the radiation to which the patients are exposed. Further, the procedure is not recommended for young women and for women who are pregnant or lactating. However, possibly the greatest limitation of mammography is that it loses its efficacy in dense breasts (mostly seen in younger women) due to the superposition of dense tissue over the mass.

MRIs have better sensitivity but this also leads to higher false-positive rates. Injecting contrast material is also invasive. Ultrasounds have lower sensitivity and are limited to detecting whether a breast mass is solid or fluid-filled. The value in detection with ultrasounds has yet to be proven and it is not considered a substitute for a screening mammogram.

Breast cancer is a global problem. To improve survival in this disease, more patients need to be identified at an early stage. With the opportunity for early detection, more lives can be saved. It is generally regarded that the main criteria for a good screening test are accuracy, high sensitivity, acceptable specificity, ease of use, acceptability to the population being screened (with regard to discomfort and time), and low cost. Existing detection methods suffer from at least one of these shortcomings, particularly in developing countries.

SUMMARY OF THE INVENTION

Disclosed is a point-of-care testing device which may be used at a patient's bedside, in emergency rooms, at outpatient clinics, in doctor offices and most conveniently, or by the patient in the comfort of her or his home. It thus provides a non-invasive, painless and easy-to-use and affordable device that allows women of all ages to safely, painlessly, and affordably screen for breast cancer throughout the year, in conjunction with annual or biannual mammography and clinical breast examination. Given the relatively acute nature of the problem in non-developed countries where significant populations of women are without widespread access to screening and detection methods such as mammography, the disclosed device may provide an easy and affordable primary diagnostic tool. In addition, the disclosed device is lightweight and portable, results are available in a very short time, e.g., about 15 minutes, or within the duration of a physician consultation, test results are shown on the device itself in a simple and user-friendly format. The disclosed devices may be readily disposed of after use. Regarding diagnostic accuracy, embodiments of the devices disclosed herein may have a sensitivity approximately of 87% and a specificity of approximately 86%.

More specifically, disclosed is a thermographic sensing device for measuring temperatures at one or more regions of the human body, particularly the breast, that utilizes a thermographic composition deposited into linear arrays of recesses formed in the lobes of a conformable medium which is disposable against the skin. The thermographic composition includes a binary solvent system and at least one colorant, wherein the compositions in each array are formulated to melt at precise temperatures, within a diagnostically temperature relevant range, to change from a first visible color to a second visible color.

According to one aspect of the disclosure, a device for measuring temperatures at one or more regions on a human breast comprises:
 a platform having a first surface and a second surface;
 a temperature sensing module disposed on the first surface of the platform, the module comprising:
  a heat conducting substrate having a top surface and a plurality of linear arrays comprising a plurality of spaced apart recesses defined in the top surface;
  a protective layer of material disposed on the top surface of the heat conducting substrate;
  a thermographic composition disposed in each recess; and
  a transparent sealing layer disposed over the heat conducting substrate to seal each recess,
 wherein the thermographic composition comprises:
  1) a binary solvent system comprising relative amounts of ortho-chloronitrobenzene (OCNB) and ortho-bromonitrobenzene (OBNB); and
  2) at least one colorant,
 wherein the relative amounts of OCNB and OBNB determine a melting point of the thermographic composition,
 wherein the thermographic composition, when in a solid state, exhibits a first color and, when in a liquid state, exhibits a second color, distinct from the first color, each of the first and second colors being visible to the naked eye.

In some embodiments, the thermographic compositions in the recesses in any one linear array are identical and have a same melting point within a diagnostically relevant temperature range.

In some embodiments, the no two linear arrays within a subset of linear arrays contain thermographic compositions with the same melting point.

In some embodiments, the different thermographic composition melting points in the plurality of linear arrays define the diagnostically relevant temperature range.

In some embodiments, alternate linear arrays of recesses have different numbers of recesses. In some embodiments, the number of recesses alternates between 7 and 15. In some embodiments, the number of recesses alternates between 8 and 14.

In some embodiments, the plurality of linear arrays of recesses comprises 18 linear arrays of recesses.

In some embodiments, the device is conformable to a shape of a human breast

In some embodiments, the thermographic compositions are formulated with respect to the relative amounts of OCNB and OBNB such that there is a difference between respective thermographic composition melting points of adjacent linear arrays in a range of 0.2° F. to 1.0° F., and in some other embodiments from 0.2° F. to 0.5° F., e.g., 0.5° F.

In some embodiments, the heat conducting material comprises metallic foil.

In some embodiments, the transparent sealing layer comprises a polyester.

In some embodiments, the diagnostically relevant temperature range is from about 88° F. to about 107° F., e.g., from about 88° F. to about 106.7° F.

In some embodiments, the diagnostically relevant temperature range is 90° F. to 98.5° F., and in some other embodiments, the diagnostically relevant temperature range is 90.5° F. to 99° F.

In some embodiments, the plurality of linear arrays of recesses is radially arranged.

In some embodiments, the linear arrays are arranged in an order corresponding to sequentially increasing thermographic composition melting points within the diagnostically relevant temperature range.

In some embodiments, each linear array comprises at least eight recesses.

In some embodiments, the platform comprises a foam material.

In some embodiments, the device further comprises:
 medical grade adhesive disposed on the first surface of the platform,
 wherein the temperature sensing module is maintained on the first surface of the platform by the adhesive.

In some embodiments, the temperature sensing module covers less than all of the first surface of the platform, and wherein the device further comprises a releasable cover layer provided over the temperature sensing module and releasably attached to the first surface of the platform by the adhesive.

In some embodiments, the first surface of the platform is divided into a plurality of lobes, and wherein the temperature sensing module is disposed on one lobe of the plurality of lobes.

In some embodiments, the linear arrays of recesses are radially arranged with respect to a center of the platform.

In some embodiments, alternate linear arrays of recesses have different numbers of recesses. In some embodiments, the number of recesses in the linear arrays alternates between 7 and 15 recesses, and in some other embodiments the number of recesses in the linear arrays alternates between 8 and 14.

In some embodiments, the plurality of linear arrays of recesses comprises 18 linear arrays of recesses.

In some embodiments, a hole is defined at a center of the foam platform and the linear arrays of recesses are radially arranged with respect to the center of the platform.

Any combination of the above embodiments, with attendant features, may be present in the device, provided that they are not inconsistent.

In some embodiments, the thermographic compositions in the recesses in any one linear array are identical and have a same melting point within a diagnostically relevant temperature range.

In some embodiments, the no two linear arrays within a subset of linear arrays contain thermographic compositions with the same melting point.

In some embodiments, the different thermographic composition melting points in the plurality of linear arrays define the diagnostically relevant temperature range.

In some embodiments, alternate linear arrays of recesses have different numbers of recesses. In some embodiments, the number of recesses alternates between 7 and 15. In some embodiments, the number of recesses alternates between 8 and 14.

In some embodiments, the plurality of linear arrays of recesses comprises 18 linear arrays of recesses.

In some embodiments, the device is conformable to a shape of a human breast.

According to another aspect of the disclosure, a device for measuring temperatures at one or more regions on a human breast comprises:
 a platform comprising foam material having a first surface and a second surface, wherein the platform is shaped to define a plurality of lobe areas;

medical grade adhesive disposed on the first surface of the platform;

a temperature sensing module disposed on each lobe area on the first surface of the platform, each module comprising:
  a heat conducting substrate disposed on the first surface of the platform, the substrate having a top surface and a plurality of linear arrays comprising a plurality of spaced apart recesses defined in the top surface;
  a protective layer of material disposed on the top surface of the heat conducting substrate;
  a thermographic composition disposed in each recess; and
  a transparent sealing layer disposed over the heat conducting substrate to seal each recess,
  wherein the thermographic composition comprises:
    1) a binary solvent system comprising relative amounts of ortho-chloronitrobenzene (OCNB) and ortho-bromonitrobenzene (OBNB); and
    2) at least one colorant,
      wherein the relative amounts of OCNB and OBNB determine a melting point of the thermographic composition,
      wherein the thermographic composition, when in a solid state, exhibits a first color and, when in a liquid state, exhibits a second color, distinct from the first color, each of the first and second colors being visible to the naked eye; and
  a releasable cover layer, having a shape corresponding to the platform, provided over the device and releasably attached to the first surface of the platform by the adhesive at the periphery.
  wherein the device is conformable to a shape of a human breast.

In some embodiments, the thermographic compositions are formulated with respect to the relative amounts of OCNB and OBNB such that there is a difference between respective thermographic composition melting points of adjacent linear arrays in a range of 0.2° F. to 1.0° F., and in some other embodiments from 0.2° F. to 0.5° F., e.g., 0.5° F.

In some embodiments, the heat conducting material comprises metallic foil.

In some embodiments, the transparent sealing layer comprises a plastic.

In some embodiments, the plurality of linear arrays of recesses is radially arranged.

In some embodiments, the plurality of linear arrays is arranged in an order corresponding to sequentially increasing thermographic composition melting points within the diagnostically relevant temperature range.

In some embodiments, each linear array comprises at least 8 recesses.

In some embodiments, the plurality of linear arrays of recesses is radially arranged with respect to a center of the platform.

In some embodiments, a hole is defined at the center of the foam platform.

In some embodiments, the diagnostically relevant temperature range is about 88° F. to about 107° F., e.g., from about 88° F. to about 106.7° F.

In some embodiments, the diagnostically relevant temperature range is 90° F. to 98.5° F., and in some other embodiments, the diagnostically relevant temperature range is 90.5° F. to 99° F.

In some embodiments, the thermographic compositions in the recesses in any one linear array are identical and have a same melting point within a diagnostically relevant temperature range.

In some embodiments, the no two linear arrays within a subset of linear arrays contain thermographic compositions with the same melting point.

In some embodiments, the different thermographic composition melting points in the plurality of linear arrays define the diagnostically relevant temperature range.

In some embodiments, alternate linear arrays of recesses have different numbers of recesses. In some embodiments, the number of recesses alternates between 7 and 15. In some embodiments, the number of recesses alternates between 8 and 14.

In some embodiments, the plurality of linear arrays of recesses comprises 18 linear arrays of recesses.

In some embodiments, the device is conformable to a shape of a human breast.

Any combination of the above embodiments, with attendant features, may be present in the device, provided that they are not inconsistent.

According to yet another aspect of the disclosure a device for measuring temperatures at one or more regions on a human breast comprises:
  a foam platform having a first surface and a second surface, wherein the platform is shaped to define three lobe areas and wherein a hole is defined at a center of the foam platform;
  medical grade adhesive disposed on the first surface of the platform;
  a temperature sensing module disposed on each lobe area on the first surface of the platform, each module comprising:
    a layer of metallic foil disposed on the first surface of the platform, the foil having a top surface and a plurality of radially arranged linear arrays comprising a plurality of spaced apart recesses defined in the top surface of the foil, wherein the linear arrays of recesses are radially arranged with respect to the center of the platform;
    a protective layer of material disposed on the top surface of the foil;
    a thermographic composition disposed in each recess; and
    a transparent plastic layer disposed over the foil to seal each recess,
    wherein the thermographic composition comprises:
      1) a binary solvent system comprising relative amounts of ortho-chloronitrobenzene (OCNB) and ortho-bromonitrobenzene (OBNB); and
      2) at least one colorant,
        wherein the relative amounts of OCNB and OBNB determine a melting point of the thermographic composition,
        wherein the thermographic composition, when in a solid state, exhibits a first color and, when in a liquid state, exhibits a second color, distinct from the first color, each of the first and second colors being visible to the naked eye; and
    a cover layer, having a shape corresponding to the foam platform, provided over the device and releasably attached to the first surface of the platform by the medical grade adhesive,
    wherein the device is conformable to a shape of a human breast.

In some embodiments, the thermographic compositions are formulated with respect to the relative amounts of OCNB and OBNB such that there is a difference between respective thermographic composition melting points of adjacent linear arrays in a range of 0.2° F. to 1.0° F., and in some other embodiments from 0.2° F. to 0.5° F., e.g., 0.5° F.

In some embodiments, alternate linear arrays of recesses have different numbers of recesses. In some embodiments, the number of recesses alternates between 7 and 15, and in some other embodiments the number of recesses alternates between 8 and 14.

In some embodiments, the plurality of linear arrays of recesses comprises 18 linear arrays of recesses.

In some embodiments, the diagnostically relevant temperature range is about 88° F. to about 107° F., e.g., from about 88° F. to about 106.7° F.

In some embodiments, the diagnostically relevant temperature range is 90° F. to 98.5° F., and in some other embodiments, the diagnostically relevant temperature range is 90.5° F. to 99° F.

Any combination of the above embodiments, with attendant features, may be present in the device, provided that they are not inconsistent.

In any of the above embodiments of the devices described in these aspects, the at least one colorant contained in the thermographic compositions may be a dye such as an organic dye which may be an oil-soluble dye, and in other embodiments, a leuco dye and in other embodiments a lactone-containing dye such as crystal violet lactone. In some embodiments, the thermographic composition may also contain an activator for a given organic dye, such as a lactone-containing dye. In some embodiments, the activator is an organic acid having a $pK_a$ of about 4 to about 12, e.g., phenol, bisphenol A, arachidic acid, pyrocathechol and 3-nitrophenol. In other embodiments, the activator is a UV absorber, e.g., 2,2', 4'4' tetrahydroxybenzophenone. In some embodiments, the compositions include a combination of the organic acid and the UV absorber.

In some embodiments, the compositions contain an organic dye. In some embodiments, the second dye is an anthroquinone dye, e.g., (1-methylamino)anthraquinone. In some embodiments, the first dye is crystal violet lactone and the second dye is an azo compound, e.g., 1-[[4-(phenylazo) phenyl]azo]-2-naphthalenol.

In some embodiments, the thermographic compositions in the recesses in any one linear array are identical and have a same melting point within a diagnostically relevant temperature range.

In some embodiments, the no two linear arrays within a subset of linear arrays contain thermographic compositions with the same melting point.

In some embodiments, the different thermographic composition melting points in the plurality of linear arrays define the diagnostically relevant temperature range.

In some embodiments, alternate linear arrays of recesses have different numbers of recesses. In some embodiments, the number of recesses alternates between 7 and 15. In some embodiments, the number of recesses alternates between 8 and 14.

In some embodiments, the plurality of linear arrays of recesses comprises 18 linear arrays of recesses.

In some embodiments, the device is conformable to a shape of a human breast.

In some embodiments, the colorant may be a pigment.

A further aspect of the disclosure a kit for differentially measuring temperatures at a plurality of locations on the human body comprises: at least one pair of devices as described hereinabove; and printed instructions for applying the at least one pair of measuring devices to the human breast tissue, and for reading the device and interpreting the results that are shown on the used devices.

According to yet another aspect of the disclosure, a you method for comparatively detecting temperature differentials in the same regions of a biological anatomy comprises: A) Providing plural similarly thermographic temperature sensing devices, each device having a temperature sensing module comprising: a heat conducting substrate having a top surface and a plurality of linear arrays comprising a plurality of spaced apart recesses defined in the top surface; a thermographic composition disposed in each recess; wherein the thermographic composition, when in a solid state, exhibits a first color and, when in a liquid state, exhibits a second color, distinct from the first color, each of the first and second colors being visible to the naked eye; B) simultaneously applying each thermographic temperature sensing devices to one of symmetrically similar regions of the biological anatomy for a time duration; and C) comparing by visual inspection of the thermographic temperature sensing devices whether a difference in color of the recesses of the plurality of linear arrays exists between two sensing devices indicating a temperature differential between symmetrically similar regions of the biological anatomy.

Other aspects of the disclosure are directed to methods of making the device, and methods of using the device to measure temperature differentials in mirror regions of breast tissue, which may allow for early breast cancer screening.

DESCRIPTION OF THE DRAWINGS

Various aspects of the disclosure are discussed below with reference to the accompanying Figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The Figures are provided for the purposes of illustration and explanation and are not intended as a definition of the limits of the disclosure. In the Figures:

FIGS. 5A and 5B are top views of a pair of devices in accordance with the disclosure, after removal from breasts, which illustrate a pattern of differential temperatures measured in mirror regions of two breasts (shown as the "A," "B" and "C" regions) following use.

DETAILED DESCRIPTION

Figure 1:
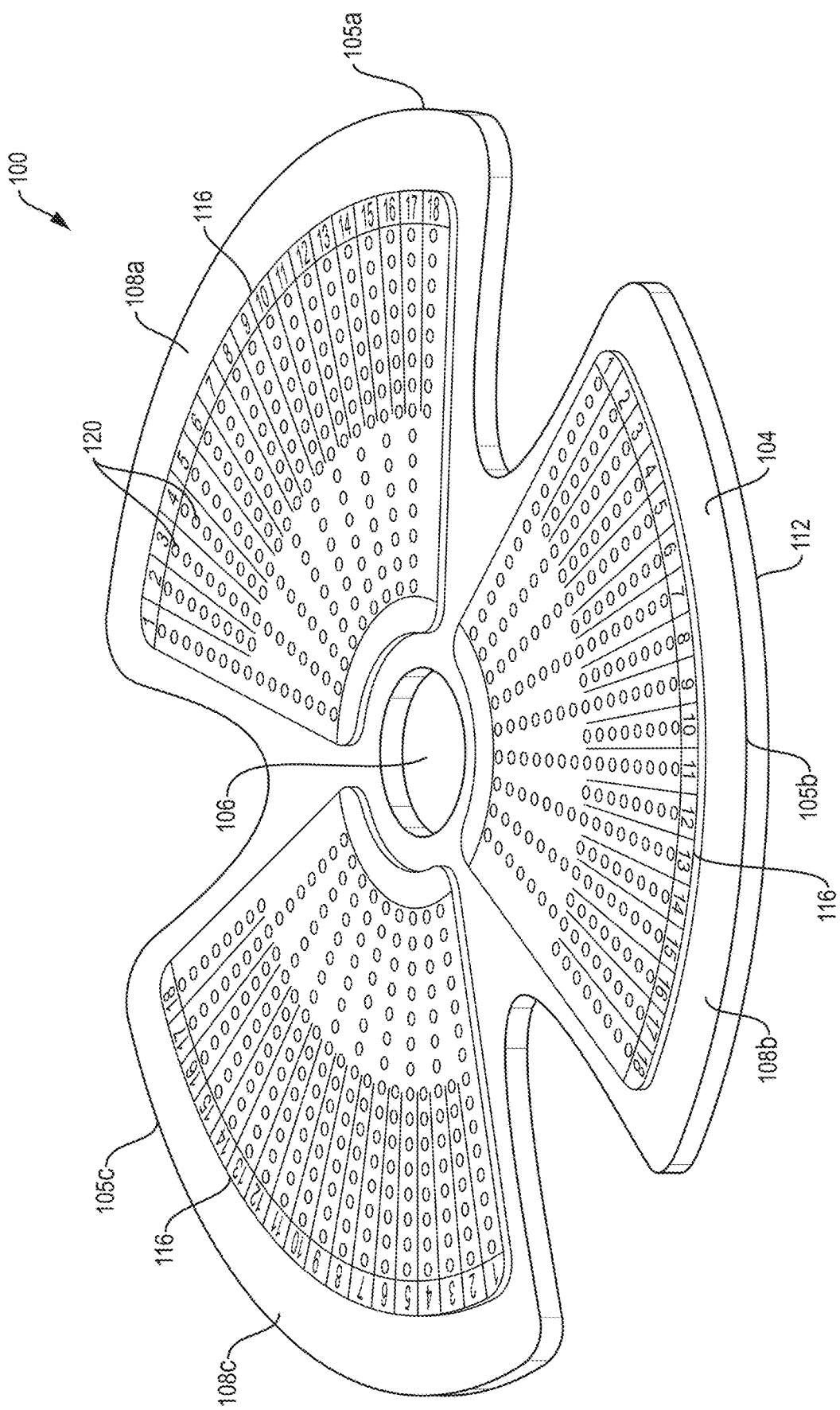
FIG. 1 is a top perspective view of an embodiment of a device of the disclosure.

It is to be understood that the disclosure is not limited in its application to the details of construction and the arrangement of the components set forth in the following description or illustrated in the drawings as it is capable of implementations or of being practiced or carried out in various ways. Also, it is to be understood that the phraseology and terminology employed herein are for the purpose of description only and should not be regarded as limiting.

Certain features, which are, for clarity, described in the context of separate implementations, may also be provided in combination in a single implementation. Conversely, various features, which are, for brevity, described in the context of a single implementation, may also be provided separately or in any suitable sub-combination.

As used herein, the term "about" means within 10% (e.g., within 5%, 2%, or 1%) of the particular value modified by the term "about."

FIG. 1 shows a device 100 for measuring temperatures in one or more regions of biological tissue, such as the human breast. The devices includes a platform 104 having a first surface 108 and a second surface 112. The platform may be made of any flexible or semi-rigid material that conforms to the breast tissue and is suitable for application and adherence of medical devices to skin. Medical grade foam tapes, which are substantially water-resistant and inert to skin, are particularly suitable in this regard. In some embodiments, platform 104 is an open or closed cell foam, which may be a polyethylene foam. The first surface 108 of platform 104 may be coated with a medical grade adhesive such as an acrylic-based adhesive. Foam padding may be obtained commercially, e.g., 3M™ 1772 Medical Foam Tape, and may include a liner, e.g., a silicone treated, polyethylene coated, bleached Kraft paper. The liner may be conveniently used as a removable/releasable cover layer for the device (shown in FIG. 2).

As also shown in FIG. 1, the device 100 contains a temperature sensing module 116 having a top surface 118 which contains a plurality of spaced-apart recesses 120 disposed thereon. A thermographic composition 216 may be disposed in each recess.

As further shown in FIG. 1, the device 100 may be disk-shaped and configured such as in the form of cut-outs or lobes 105a, 105b and 105c, to contain multiple temperature sensing modules e.g., 2, 3 or 4, each of which may have a temperature sensing module 116 disposed thereon. This arrangement facilitates application of the device to the breasts without any wrinkling or folding of the device, and for simultaneous temperature measurements in a plurality of regions of the breast. The relative dimensions of the platform and the module(s) may vary so as to allow for a periphery 108A, 108B and 108C of the first surface of the platform that is not covered by the module(s) to facilitate adhering the device to the tissue. Device 100 may further include a nipple hole 106, that defines the center of the device, and which also facilitates application of the device to a breast.

The device 100 may be made in various convenient shapes and in sizes, typically ranging from about 5 inches to about 9 inches (e.g., 5, 6, 7, 8 or 9 inches) in overall diameter, in order to accommodate a wide variety of breast sizes, and depending upon the number of regions of breast tissue to be measured. Overall thickness of the device typically ranges from about 3 mm to about 4 mm, and in some embodiments from about 3.25 mm to about 3.75 mm, e.g., about 3.5 mm. The device itself, and advantageously all the individual structural elements therein, are flexible and easily conform to the contour of a wide variety of human breasts, male and female alike, to maximize contact between the device and the breast tissue. Although not shown, the device may include one or two appropriately shaped lobes with corresponding temperature sensing modules (that would measure temperatures of mirror hemispheric regions of left and right breast tissue) or more than three, e.g., 4, appropriately shaped lobes with corresponding temperature sensing modules (that would measure temperature of mirror quadrant regions of breast tissue). The lobes may be substantially equal in size.

Figure 2:
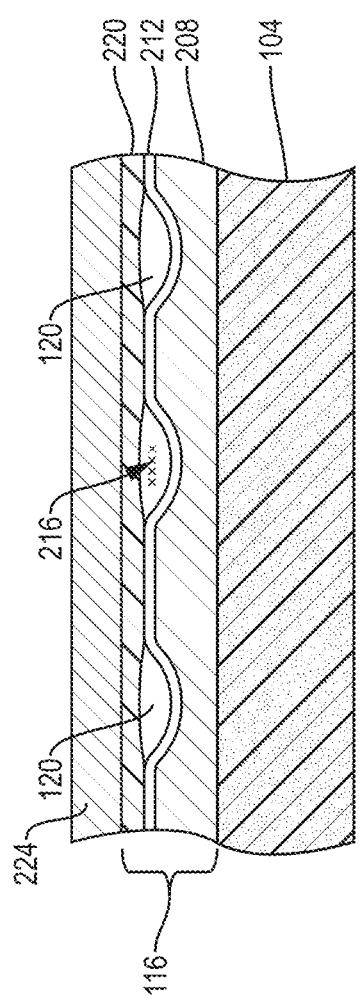
FIG. 2 is a partial cross-sectional view of a device of the disclosure.

As shown in FIG. 2, the temperature sensing module 116 includes a heat-conductive substrate 208 having a top surface and with the plurality of linear arrays of spaced apart recesses 120 defined in the top surface. The conductive nature of the substrate 208 provides substantially uniform distribution of heat that emanates from the breast tissue to each array and the recesses contained therein. The substrate 208 may be a layer of a heat-conductive metal foil, such as an aluminum foil (wherein the metal may be in the form of an alloy). Aside from aluminum, flexible, heat-conductive sheets of other materials such as, for example, copper, silver, gold, stainless steel and any other heat-conductive pliable materials, may also be useful. The heat conducting substrate may have a thickness that accommodates the depth of the recesses 120. The thickness of the heat conducting substrate typically varies from about 0.0015 to about 0.0025 inches.

As shown in FIG. 2, the temperature sensing module 116 also contains a protective layer 212 that is disposed on the top surface of the heat conducting substrate 208 (and which may constitute the top surface of the temperature sensing module 116). The protective layer 212 may be composed of a thermoplastic polymer or copolymer, examples of which include polyesters such as polyether terephthalate (commercially available under the tradename Mylar®), ethylene copolymers (commercially available under the tradename Surlyn®) and polyamides such as nylon. The protective layer 212 serves to prevent or minimize contact between the heat conducting substrate 208, particularly metallic foils, and the thermographic compositions 216, which tend to be corrosive. The protective layer 212 may be disposed on and secured to the heat conducting substrate 208 via adhesive, e.g., a polyurethane adhesive. The protective layer 212 has a thickness that typically varies from about 0.0005 to about 0.0015 inches.

Referring again to FIG. 2, the recesses 120 have a round or circular shape and a depth such that they will accommodate volumes (of thermographic compositions) that typically ranges from about 250 nl to about 400 nl. Thus, the depth of the recesses 120 typically varies from about 0.001 inches to about 0.002 inches and in some embodiments about 0.0015 inches. The number of recesses in the linear array 120 may vary, e.g., from about 2 to about 20, and in some embodiments each linear array has at least 3, 4, 5, 6, 7 or 8 recesses. The number of recesses in each linear array may differ. For example, alternating linear arrays may have between 3-8 recesses and 12-15 recesses. In some other embodiments, the number of recesses in each linear array may alternate between 7 and 15 recesses, and in yet other embodiments, between 8 and 14 recesses.

The temperature sensing module 116 may be prepared by methods known in the art, such as by first adhering the protective layer 212 to the heat conducting substrate 208 and then subjecting the product to a dimpling process. The module 116 may be treated beforehand in order to enhance the adhesion of the thermographic compositions 216 in the recesses. A corona treatment may suffice in these regards. Thermographic compositions, in liquid form, are dispensed in the recesses in each of the columns in the array, typically in a volume of about 275 nanoliters (nl) to about 375 nl. Once the compositions are dispensed in the recesses, the temperature sensing module 116 containing the thermographic compositions 216 may be passed through a chilling chamber to quickly freeze and solidify the compositions.

As shown in FIG. 2, the device further includes a transparent sealing layer 220. This layer 220 seals each recess 120 and the thermographic compositions 216 disposed therein. The sealing layer 220 is advantageously impermeable to the thermographic compositions 216. The transparency of the sealing layer 220 permits ease of reading the device after removal of the device from breast tissue. Polyisobutylene (PIB)-based materials are suitable. PIB-type adhesives are commercially available from BASF under the tradename Oppanol® B (known as a series of medium and high molecular weight polyisobutenes having a weight-average molecular weight (Mw) between 40,000 and 4,000,000), and Chevron Chemical Co. Other materials that may be used as the sealing layer 220 include polypropylene, polyethylene terephthalates, nitrocellulose and polyvinyl chloride. The sealing layer 220 may be applied and sealed to the top surface of the temperature sensing module 116 in the form of a laminate and via procedures known in the art such as heat or vacuum sealing. In some embodiments, the opposing or outer surface transparent sealing layer 116 may have medical grade adhesive disposed thereon.

In the practice of making the device 100, the transparent protective layer 220 is applied to the heat conducting module 116, the recesses having been filled with the thermographic compositions 216 in liquid form, thus making a composite. The resulting composites may be die cut in order to produce a plurality of substantially equally shaped segments, e.g., triangular segments, followed by applying the segments to the corresponding number of lobe areas 105 on the first surface 108 of the platform 104.

As shown in FIG. 2, the device 100 may further include a removable cover layer 224, which may be made from silicon-treated paper such as siliconized Kraft paper. This layer 224, which may cover the entirety of the device 100, protects the device 100 after manufacture and prior to use. In some embodiments wherein the platform 104 material is commercially available in combination with a so-called release liner, the liner may conveniently serve as the removable cover layer. The removable cover layer 224 maybe adhered to the device 100, e.g., by adhesive disposed on the periphery 108A of the first surface 108 of the platform 104 that is not covered by the temperature sensing module(s). The resulting device 100 may then be die cut (consistent with the number and shape of the temperature sensing module(s)) into the final shape of the device 100. The removable cover layer 224 is easily removable prior to application of the device 100 to the breast tissue.

Since breasts are an appendage to the body, they have a lower temperature than the normal body temperature of 98.6° F. The actual temperature depends on the size and shape of an individual's breasts. In normal, non-diseased situations, the temperature is substantially the same for both breasts. When early stage breast cancer or certain forms of breast disease is present, however, metabolic activity increases, producing increased heat in the affected breast. As is known in the art, the likelihood of having a cancerous condition in the same region in both breasts is small. The device disclosed herein measures the temperature difference in at least one mirrored region of each breast, i.e. the same region in each respective breast. By comparing temperature readings from one breast to the other, the disclosed device can quantify unilateral variations in temperature as between mirror regions of the breasts. A temperature difference of 2° F. or more between mirror-image regions may indicate that a pathologic condition exists in the breast with the elevated temperature.

The thermographic compositions 216 are solid solutions at room temperature, and at higher temperatures, including temperatures in a diagnostically relevant temperature range, undergo a change in state from solid to liquid. The thermographic compositions 216 exhibit a first color in the solid state, which is visible to the naked eye, and exhibit a second color when in the liquid state, which color is distinct from the first color and is also visible to the naked eye.

The thermographic compositions 216 include a binary solvent system, and at least one colorant. The binary solvent system includes a mixture of ortho-bromonitrobenzene (OBNB), which has a melting point of 106.88° F., and orthochloronitrobenzene (OCNB), which has a melting point of 90.98° F. The relative amounts of each solvent in the solid state (which may be measured by weight) may be varied in a given thermographic composition 216 such that the composition melts, with an accompanying color change, at a precise temperature within the range. The thermographic compositions 216 also possess the property of stable undercooling and will remain liquid for at least several minutes up to several hours when subjected to a surrounding temperature that is somewhat below the melting point of the composition. This property allows for ease of reading and interpreting the results without haste due to the supercooling effect of the binary system.

Given the variability in normal and diseased breast tissue, the thermographic compositions 216 may be formulated to have precise melting points over the diagnostically relevant temperature range. Broadly, this range may include temperatures from about 88° F. to about 107° F., e.g., from about 88° F. to about 106.7° F. (the upper end taking into account high fever), in order to detect breast disease such as cancer. In some embodiments, the device is configured to detect breast temperatures in a range of about 90° F. to about 99° F., and in some embodiments from about 90° F. to about 98.5° F., and in some other embodiments from about 90.5° F. to about 99° F.

In order to accurately detect temperatures throughout this range, thermographic compositions contained in any one linear array 120 contain the same relative amounts of OBNB and OCNB, and thus have the same melting point. The melting point temperatures of the thermographic compositions 216 are typically accurate to within ±0.2° F. Also, no two linear arrays within a subset of linear arrays contain thermographic compositions 216 having the same melting point. The compositions contained in each successive linear array within a subset of linear arrays are thus formulated by varying the relative amounts of OBNB and OCNB (which due to their respective melting points are inversely related, and which also may be measured in terms of weight in the solid state), such that the compositions in each successive array have incrementally increasing melting points, typically in increments of about 0.2° F. to about 1.0° F., and in some embodiments from about 0.2° F. to about 0.5° F., and in some embodiments about 0.25° F., and in yet other embodiments about 0.5° F. The number of linear arrays disposed in the temperature sensing module 116 will be determined in accordance with the shape of the surface to which the device is to conform. For example, for a device intended for use with the human breast, for 1.0° F. increments over a range of 90°–99° F., inclusive, the device may contain 10 linear arrays, and for 0.5° F. increments, the device may contain 19 linear arrays. The relative amounts of OBNB may thus vary from about 6% (at the lower end of the temperature range) to about 75% (wt/wt) (at the higher end of the temperature range) and in some embodiments from about 12.5% to about 72%. The relative amounts of OCNB may vary from about 95% to about 25% (wt/wt) and in some embodiments from about 88% to about 28%.

The thermographic compositions 216 also contain at least one colorant. The colorant is compatible with (e.g., soluble or dispersible in) the liquid resulting from the change of state from solid to liquid. In some embodiments, it is soluble in the solvent system when the composition is in the liquid state, and which causes a change in color of the composition, which is visible to the naked eye, when the composition changes from solid to liquid and from liquid to solid. The presence of the colorant allows the compositions 216 to reflect or absorb light in the visible area of the spectrum on or below the melting point of the solvent system or, in the alternative, on or above the melting point of the solvent system, or both in different colors, so that a change in color is visible to the naked eye. The colorant may be a dye such as an organic dye. Oil-soluble dyes are suitable.

In some embodiments, the compositions contain a leuco dye, which as known in the art, exists in two forms, one of which is substantially colorless. Examples of leuco dyes include dyes that contains a lactone group such as crystal violet lactone. Some lactone-containing dyes, such as crystal violet lactone, are leuco dyes.

Representative examples of anthraquinone dyes that may be useful with practice of the disclosed device include anthraquinone dyes substituted once or severally with one or more of the following functional groups: amino, alkylamino, arylamino, acylamino, aroylamino, aroylamino wherein the aryl ring is further substituted, alkylsulfonylamino, alkylsulfonylamino wherein the alkyl chain may be branched and contains from two to twenty carbons atoms, arylsulfonylamino, arylsulfonylamino wherein the aryl ring is further substituted, hydroxy, alkoxy, aryloxy, substituted aryloxy, alkylthio, arylthio, substituted arylthio, chloro, bromo, etc.

Representative examples of azo compounds that can be used as dyes that may be useful with practice of the disclosed device include 1-[[4-(phenylazo)phenyl]azo]-2-naphthalenol, 1-(Phenyldiazenyl)naphthalen-2-ol, 1-(2,4-Dimethylphenylazo)-2-naphthol, 1-[{2-Methyl-4-[(2-methylphenyl)diazenyl]phenyl}diazenyl]naphthalen-2-ol, sodium 4-(2-hydroxy-1-naphthalenylazo)-naphthalenesulfonate, sodium 4-[(E)-(4-anilinophenyl)diazenyl]benzenesulfonate, sodium 4-[(2E)-2-(2-oxonaphthalen-1-ylidene) hydrazinyl]benzenesulfonate, sodium 2-hydroxy-5-[(E)-(4-nitrophenyl)diazenyl]benzoate, alcian yellow, allura red AC, trisodium (4E)-3-oxo-4-[(4-sulfonato-1-naphthyl) hydrazono]naphthalene-2,7-disulfonate, 1-(2,5-Dimethoxy-phenylazo)-naphthalen-2-ol, disodium 5-amino-4-hydroxy-3-(phenylazo)-naphthalene-2,7-disulfonate, 1-(2,5-dimethyl-4-(2,5-dimethylphenyl) phenyldiazenyl) azonapthalen-2-ol, mordant red 19, 1-[(E)-(4-Nitrophenyl)diazenyl]-2-naphthol, ponceau 2R, ponceau 3R, ponceau 4R, sirius red, or N-Ethyl-1-((4-phenyldiazenyl)phenyl)diazenyl)naphthalen-2-amine.

Yet other examples of dyes that may be useful with practice of the disclosed device include quinolone dyes, e.g., pinacyanol chloride, pinacyanol bromide, pinacyanol iodide, quinaldine red, cryptocyanine, 1,1'-Diethyl-2,2'-cyanine iodide, 2-(p-Dimethylaminostyryl)-1-ethyl-pyridinium iodide, 3,3'-Diethylthiadicarbocyanine iodide, ethyl red, Dicyanine A, Merocyanine 540™ and Neocyanine™.

Further examples of dyes that may be useful with practice of the disclosed device include sulphonephthalein dyes, e.g., cresol red, chlorophenol red, chlorophenol blue, bromophenol blue, bromocresol purple and chlorocresol green. Further representative examples of organic dyes that may be useful with practice of the disclosed device, such as Sudan dyes, are generally known in the art. See, e.g., U.S. Pat. No. 4,232,552, the contents of which are hereby incorporated by reference in their entirety for all purposes.

In some embodiments, the thermographic compositions 216 contain a plurality of (e.g., two) dyes, both of which may be organic dyes. The respective dyes may or may not exhibit visible color in both the solid and the liquid states, provided, however, that the compositions exhibit a first color in the solid state and a second, distinct color in the liquid state, wherein the colors are visible to the naked eye. For example, a composition containing the leuco dye crystal violet lactone exhibits a very bright blue color in a solid state and a faint yellow color in the liquid state. The presence of a second organic dye that dominates the overall color of the composition when in the liquid state, may further enhance reading and interpretation of the results. For example, the composition may include a dye that exhibits a strong red color when in the liquid state, such that upon melting the compositions change from blue to red.

The thermographic compositions 216 may contain additional components. For example, as is known in the art, some dyes are pH-sensitive and are used in combination with an activator or developer. Some dyes containing lactone groups, e.g., crystal violet lactone, may be used with an activator. Representative examples of activators include organic acids having a $pK_a$ of about 4 to about 12, e.g., phenol, bisphenol A, arachidic acid, pyrocathechol and 3-nitrophenol. Other examples of activators include UV absorbers, e.g., 2,2',4'4'-tetrahydroxybenzophenone (commercially available from BASF under the tradename Uvinul®). The total amount of the activator(s) generally varies from about 0.25% to about 0.70%, based on the total weight of the thermographic composition.

The colorants, and other non-solvent components of the compositions may be referred to as an indicator system. In some embodiments, the colorant may include a pigment. The amounts of the colorant(s) and the indicator system contained in the thermographic compositions 216 may be determined in accordance with standard techniques, in order to obtain visible color change in the volumes of solvent accommodated by the recesses. The amount of colorant typically varies from about 0.10% wt to about 0.40% wt, and the amounts of the indicator system typically vary from about 0.1% to about 1.0% by weight, based on the total weight of the composition.

Figure 3:
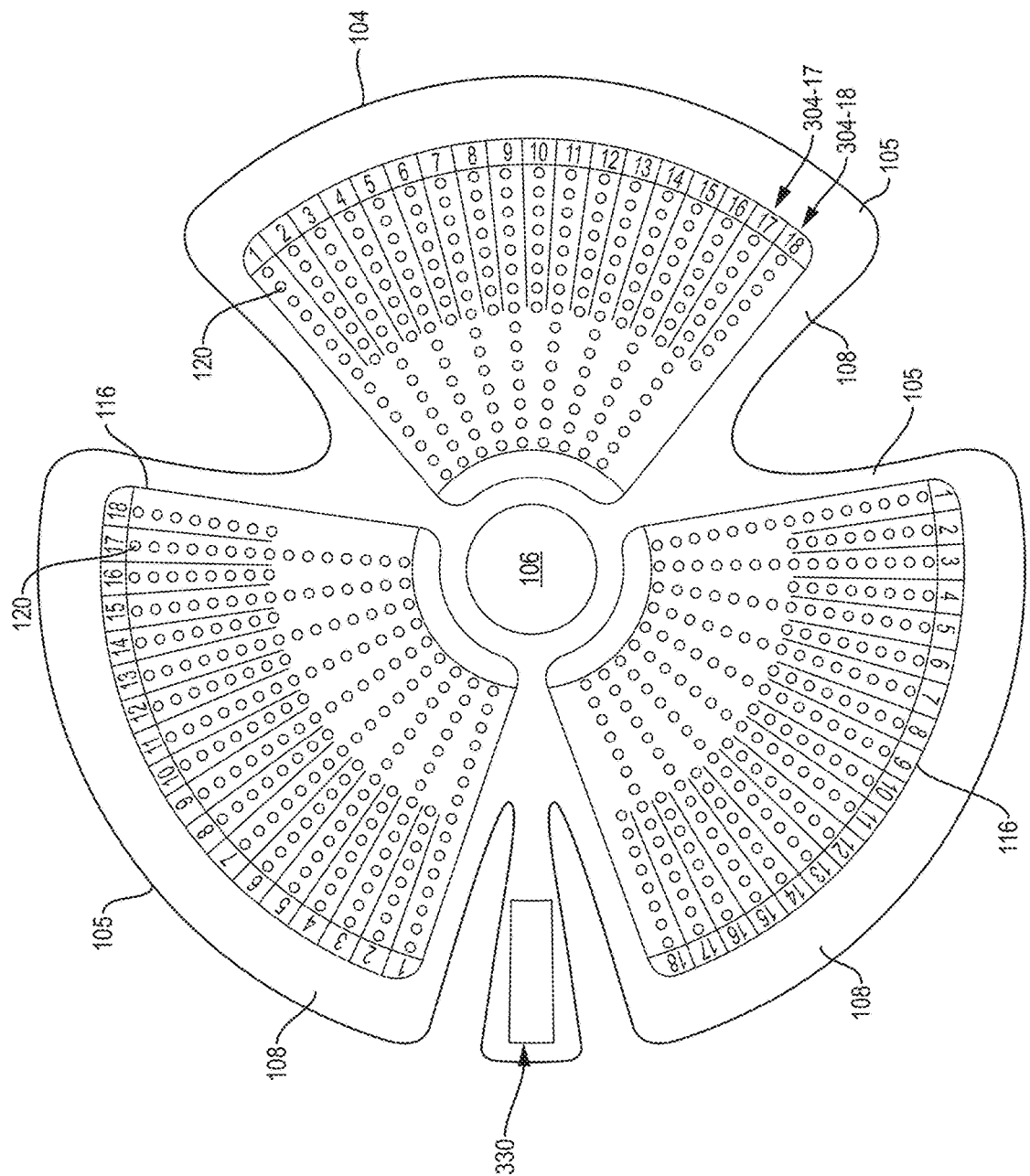
FIG. 3 is a top view of a device of the disclosure.

As a non-limiting example, shown in FIG. 3, 18 linear arrays are present in each segment, wherein successive arrays include alternating columns of 14 and 8 recesses. This design and configuration may accommodate spatial constraints of the device. The linear arrays cover a temperature range of 90-98.5° F. As shown, the device 100 contains 3 temperature sensing modules 116 A, B and C, disposed in the respective lobes 105 on the first surface 108 of the platform 104. Each temperature sensing module 116 contains 18 linear arrays 304, of spaced apart recesses 120. The arrays contain alternating numbers of 14 and 8 recesses. This device is particularly suitable for measuring temperatures in increments of 0.5° F., over a range of about 9° F., e.g., 90-98.5° F., or 90.5-99° F. In some other embodiments, the device may contain 19 arrays so as to measure temperatures in the range of 90-99° F. The thermographic compositions 216 contained in the recesses 120 in each of the arrays may be formulated, in terms of relative amounts (expressed in terms of % wt/wt) of OBNB and OCNB present therein, as set forth in Table 1.

As reflected in Tables 1-5 below, relative amounts of OBNB and OCNB and the amounts of components in the indicator system (colorant(s) and activator(s)) may be determined in accordance with standard laboratory techniques. Due to potential impurities in the compounds and variability in the sensitivity of instruments, Tables 2 and 3 provide ranges for the colorant(s) and activator(s).

TABLE I

TEMPERATURE DIFFERENTIAL FORMULA

| Array No. | Corresponding Melting Point Temperature ° F. | Percent Weight/Weight O-BROMONITROBENZENE to O-CHLORONITROBENZENE | |
|---|---|---|---|
| 1 | 90.0 | 12.74 | 87.26 |
| 2 | 90.5 | 18.74 | 81.26 |
| 3 | 91.0 | 23.54 | 76.46 |
| 4 | 91.5 | 28.04 | 71.96 |
| 5 | 92.0 | 32.14 | 67.86 |
| 6 | 92.5 | 36.04 | 63.96 |
| 7 | 93.0 | 39.54 | 60.46 |
| 8 | 93.5 | 43.24 | 56.76 |
| 9 | 94.0 | 46.84 | 53.16 |
| 10 | 94.5 | 50.44 | 49.56 |
| 11 | 95.0 | 53.24 | 46.76 |
| 12 | 95.5 | 56.04 | 43.961 |
| 13 | 96.0 | 58.84 | 41.16 |
| 14 | 96.5 | 61.64 | 38.361 |
| 15 | 97.0 | 64.44 | 35.56 |
| 16 | 97.5 | 67.04 | 32.96 |
| 17 | 98.0 | 69.24 | 30.76 |
| 18 | 98.5 | 71.94 | 28.06 |
| 19 | 99.0 | 74.90 | 25.10 |

In some embodiments, the indicator system may include the following dyes and activators, in amounts in the ranges set forth in Tables 2 and 3 below.

TABLE 2

| | |
|---|---|
| COPIKEM I (Crystal Violet Lactone) | (0.10 and 0.3% wt) |
| 2,2',4'4'-tetrahydroxybenzophenone (Uvinul) | (0.10 and 0.3% wt) |
| 1-methylaminoanthraquinone (Spectra III) | (0.04 and 0.05% wt) |
| 4,4'-isopropylidenediphenol (Bisphenol A) | (0.10 and 0.3% wt) |

TABLE 3

| | |
|---|---|
| COPIKEM I (Crystal Violet Lactone) | (0.10 and 0.3% wt) |
| 2,2',4'4'-tetrahydroxybenzophenone (Uvinul) | (0.10 and 0.3% wt) |
| 1-[[4-(phenylazo)phenyl]azo-2-naphthalenol (D&C Red #17) | (0.03 and 0.05% wt) |
| 4,4'-isopropylidenediphenol (Bisphenol A) | (0.10 and 0.3% wt) |
| Arachidic Acid | (0.01 and 0.03% wt) |

By way of representative example, 19 thermographic compositions, each designed to melt at 0.5 degree increments in a range from 90 degrees to 99 degrees as shown in Table 1, may be prepared by mixing together relative amounts of an ortho-chloro composition and an ortho-bromo composition, as shown in Tables 4 and 5, respectively.

TABLE 4

| | Wt % |
|---|---|
| Ortho-Chloro (Mother) Mix | |
| Ortho-chloronitrobenzene | 99.40% |
| 2,2',4'4'-tetrahydroxybenzophenone (Uvinul) | 0.20% |
| 4,4'-isopropylidenediphenol (Bisphenol A) | 0.20% |
| COPIKEM I (Crystal Violet Lactone) | 0.15% |
| 1-methylaminoanthraquinone (Spectra III) | 0.05% |
| Ortho-Bromo (Father) Mix | |
| Ortho-bromonitrobenzene | 99.40% |
| 2,2',4'4'-tetrahydroxybenzophenone (Uvinul) | 0.20% |
| 4,4'-isopropylidenediphenol (Bisphenol A) | 0.20% |

TABLE 4-continued

| | Wt % |
|---|---|
| COPIKEM I (Crystal Violet Lactone) | 0.15% |
| 1-methylaminoanthraquinone (Spectra III) | 0.05% |

TABLE 5

| | Wt % |
|---|---|
| Ortho-Chloro (Mother) Mix | |
| Ortho-chloronitrobenzene | 99.39% |
| 2,2',4'4'-tetrahydroxybenzophenone (Uvinul) | 0.15% |
| 4,4'-isopropylidenediphenol (Bisphenol A) | 0.25% |
| COPIKEM I (Crystal Violet Lactone) | 0.15% |
| 1-[[4-(phenylazo)phenyl]azo-2-naphthalenol (D&C Red #17) | 0.04% |
| Arachidic Acid | 0.02% |
| Ortho-Bromo (Father) Mix | |
| Ortho-bromonitrobenzene | 99.39% |
| 2,2',4'4'-tetrahydroxybenzophenone (Uvinul) | 0.15% |
| 4,4'-isopropylidenediphenol (Bisphenol A) | 0.25% |
| COPIKEM I (Crystal Violet Lactone) | 0.15% |
| 1-[[4-(phenylazo)phenyl]azo-2-naphthalenol (D&C Red #17) | 0.04% |
| Arachidic Acid | 0.02% |

Figure 4:
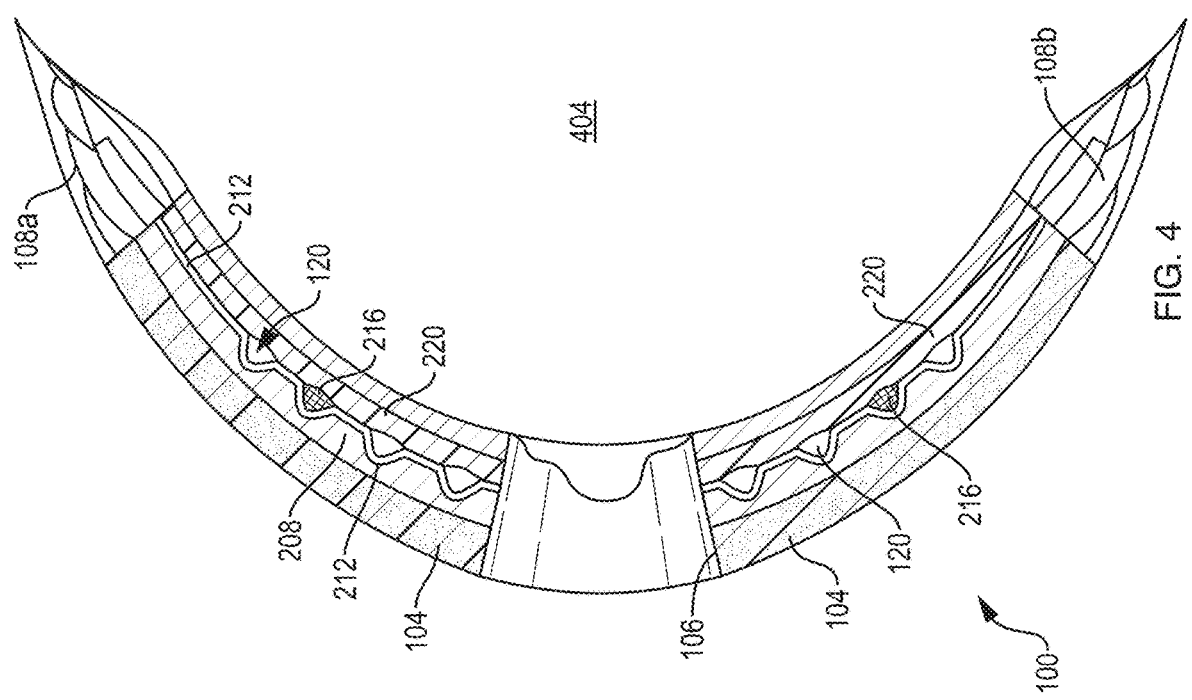
FIG. 4 is a cross-sectional view of a device of the disclosure, as applied to a human breast in accordance with disclosure.

As shown in FIG. 3, device 100 further includes a data structure 330 which may attached to the first surface 108 of the platform 104. In embodiments, data structure 330 may be implemented with a QR code which is a machine-readable code that includes an array of black and white regions, typically used for storing URLs or other information for reading by the camera on a smartphone. The QR code may be used to convey other data about the device, such as a serial number for the device for establishing authenticity in terms of commercial source, and tracking production details such as the lot or batch number, and which may be used in communication with an electronic device to read the results. Other data structure formats such as two and three-dimensional barcodes may be similarly utilized for data structure 330 with the devices disclosed herein A cross-sectional view of a device 100 once applied to the breast 404 (minus the second backing layer which is removed beforehand), is shown in FIG. 4. In practice, the disclosed device 100 is applied to each breast 404. Thus, a pair of devices 100 may be packaged together in the form of a kit, sealed so as to be substantially impermeable to air, along with printed instructions for use, e.g., proper alignment of each device on the breasts so that the mirror regions of each breast are matched with corresponding lobe areas of the device, and for reading and interpreting the results shown on the used device after it is removed from the breast. The kit may be stored at temperatures suitably below the diagnostically relevant temperature range, e.g., below 80° F.

The device 100 may not require the assistance of a practitioner, such as a physician or nurse. The patient may apply the device herself. The patient may be seated in an upright position. The removable (releasable) cover layer (not shown) is removed. First placing the nipple hole 106 over the nipple, enabling the nipple to protrude from nipple hole, the device 100 is applied (e.g., pressed onto) the breast 404 such that the device is adhesively secured to the breast. The procedure is repeated for the other breast. Although not shown in the figure, the devices are applied in the same alignment, in which the designated lobes A, B and C, are placed on the corresponding mirror regions of the breasts. In this fashion, the measuring and comparing temperature differences in more than one, e.g., three regions of the breast, serves as a control. Further, once the thermographic composition in one or more of the columns melts and becomes liquid, the color will change. For example, in the case of compositions containing crystal violet lactone and Spectra III, the color turns from blue to red, enhancing ease of reading and interpreting the results. The application of the device to both breasts is advantageously performed in less than about two minutes so as to minimize conversion of the thermographic compositions to the liquid state prior to contact with the breast tissue, and thus ensure accurate results. FIG. 4 shows the device 100 fitted onto the breast 404, centered via the nipple hole 106. Transparent plastic layer 220 is contiguous to the breast tissue. The device 100 may be adhesively and releasably secured to the breast tissue via the overlapping portions or peripheries 108A and 108B of the platform 104 via the adhesive disposed on the first surface 108 thereof (periphery 108C not shown).

The devices may be in place for about 15 minutes. Thereafter, the devices are removed for purposes of reading and interpreting the results.

The following provides an embodiment regarding the recordation and interpretation of the results, in the context of a device 100 having three segments of the heat conductive substrate and using thermographic compositions described in Table 1 and which contain crystal violet lactone and Spectra III.

FIGS. 5A and 5B show devices 500 and 550 removed from the left and right breasts, respectively. The numbers 1-18 printed on each temperature sensing module 116 signify the number of linear arrays where each array represents a specific temperature within the range of 90-98.5° F., from lowest to highest, and in increments of 0.5° F. The letters A, B and C signify the lobes that will be positioned on the same region of each breast for purposes of correctly aligning each device 500 and 550, e.g., so that lobe A will be positioned on the top of each breast, lobe B is positioned on the inner breast, and lobe C is positioned on the outer breast). For purposes of the figures, the color change is shown by light or dark recesses or dots, where dark dots signify that the thermographic compositions therein melted and thus changed color from blue to red. A test recording form may be placed next to the left and right devices. Lines 504A, 504B, 504C and 554A, 554B and 554C may be drawn on the Test Recording Form (or on the used devices themselves) from the top (where the numbers 1-18 are printed) to the bottom (where the letters A, B and C are printed on the highest numbered array showing a change of color (i.e., from light (blue) to dark (red)) in at least three recesses. This is done for each of the three regions, in both of the left and right breast pads. Once each of the three regions on both the left and right device have been read and marked with respective lines 504A-C and 554A-C, the array number that the line is drawn through for each of the three regions for each breast on the bottom of the form is recorded. The difference for each mirror region is calculated. The difference in the array numbers between the A region in the left breast pad and the corresponding A region in the right breast pad determines the temperature differential. The same holds true for the B and C regions in determining the temperature differential. The results of the A, B and C regions are read and interpreted individually.

In a healthy breast, the temperature of both breasts is substantially the same. Thus, in a non-pathological situation, the tissue in each of the mirror regions of both breasts will be about equal, e.g., within 2.0° F. within each other. Assuming that for an individual patient, the temperature of the one region of the breast tissue is 93.0° F., the thermographic compositions contained in at least three of the recesses in each of linear arrays enumerated 1-7 contained in the same lobe on both breasts will turn from light to dark (e.g., blue to red). In contrast, if the tissue of one breast has increased metabolic activity, the temperature will be higher and a color change will appear in at least one higher numbered linear array.

In FIG. 5A, the highest numbered column with at least three dark recesses is row 5, which means that the temperature of this "A" region of the left breast is 92° F. In FIG. 5B, the highest numbered column with at least three dark recesses is row 9, which means that this mirror "A" region of the right breast is 94° F. A difference of 4 or more lines or columns, which represents a temperature differential of 2° F. or more, may be considered diagnostically significant. This result will constitute an alert and the user may consult with a doctor for further tests.

Figure 6:
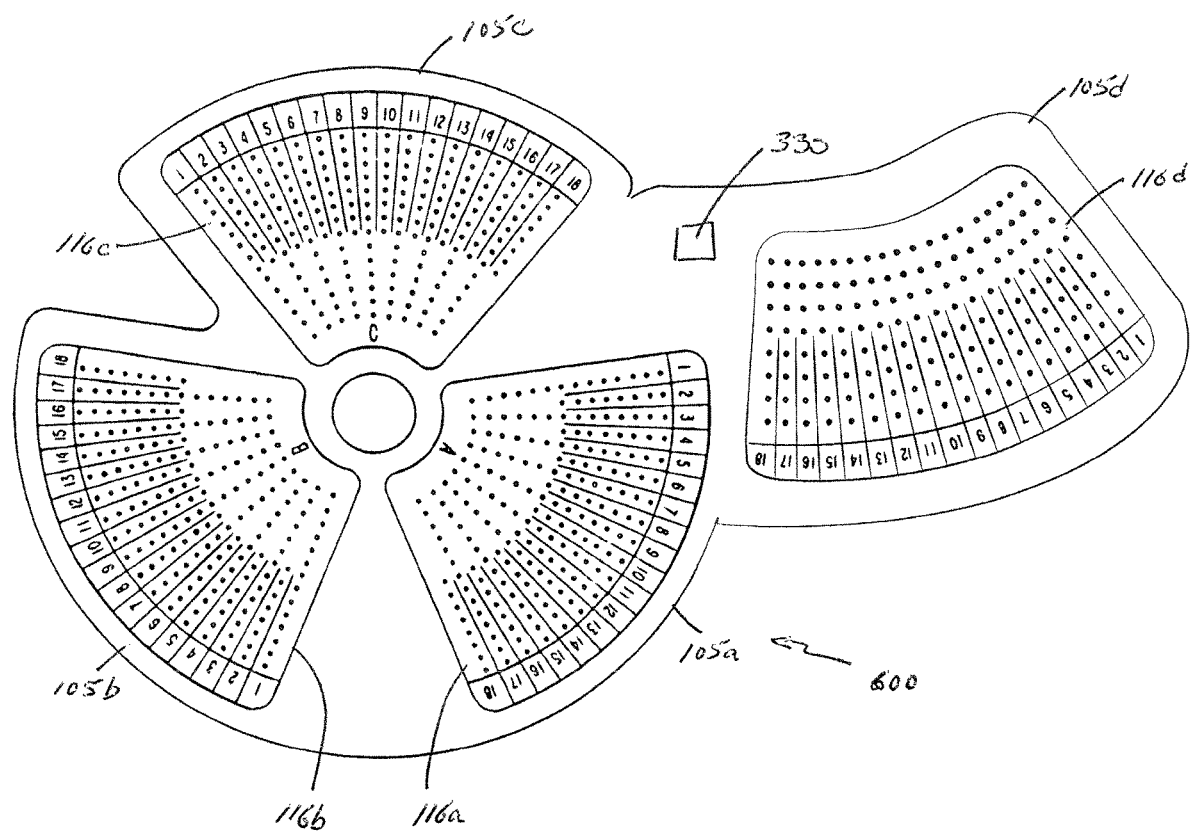
FIG. 6 is a top view of an embodiment of a device of the disclosure device of the disclosure.

FIG. 6 is a top view of an embodiment of a device 600 substantially similar in construction and function as device 100 described herein with reference to FIGS. 1-5B, except that device 600 further comprises an additional lobe 105d having a temperature sensing module 116d disposed thereon, as illustrated. The device 600, when placed over the breast, enables the lobe 105d to be positioned approximately underneath the armpit for detection of heat signatures by temperature sensing module 116d in the area of any lymph nodes proximate the armpit. The temperature sensing module 116d may have a similar or different construction and function to temperature sensing module 116a-c described herein. Specifically, the arrangement and pattern of recesses 120 of temperature sensing module 116d on lobe 105d may be different than that of lobes 105a-c and may be designed for optimal coverage of the desired area. In addition, the space intermediate lobe 105d and the closest adjacent lobes 105a and 105c may be approximately as illustrated or may be increased or decreased. Similar to devices 500 and 550, the device 600 may also include a data structure 330, which may be implemented with a QR code, similar to devices 500 and 550.

In another embodiment, any of devices 500, 550 and 600 may be combined into a kit containing diagnostic constructions in addition to at least one or multiple devices. For example, a pair of devices 500 may be packaged as a kit along with an instructional materials on how to utilize the devices. Regarding device 600, such a kit would include two devices 600, each of which has a perimeter shape which may be the symmetric reflection of the other so that the lobe 105d and its corresponding temperature sensing module 116d are oriented properly approximately underneath the armpit for detection of heat signatures in the area of any lymph nodes proximate the armpit.

At various places in the present specification, values are disclosed in groups or in ranges. It is specifically intended that the description include each and every individual subcombination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Similarly, for example, a real number in the range of 0.00 to 40.00 is specifically intended to individually disclose all real numbers between 0.00 and 40.00.

Although the invention described herein has been described with reference to particular embodiments, it is to be understood that these embodiments are merely illustrative of the principle and applications described herein. It is therefore to be understood that numerous modifications may be made to the illustrative embodiments and that other arrangements may be devised without departing from the spirit and scope of the various embodiments described herein as defined by the amended claims.

What is claimed is:

1. A device for measuring temperatures at one or more regions on a human, the device comprising:
    a platform having a first surface and a second surface, wherein the platform is shaped to define a plurality of lobe areas wherein each of the plurality of the lobe areas is conformable to a shape of a human breast, and wherein a hole is defined at a center of the platform;
    a temperature sensing module disposed on each lobe area of the first surface of the platform, the module comprising:
        a heat conducting substrate comprising metallic foil, the substrate having a top surface and a plurality of linear arrays, each array comprising a plurality of spaced apart recesses, defined in the top surface;
        a protective layer of material disposed on the top surface of the heat conducting substrate;
        a thermographic composition disposed in each recess; and
        a transparent sealing layer disposed over the heat conducting substrate to seal each recess,
        wherein the thermographic composition comprises:
            a binary solvent system comprising relative amounts of ortho-chloronitrobenzene (OCNB) and ortho-bromonitrobenzene (OBNB);
            a first dye comprising crystal violet lactone which is present in an amount of 0.1% to 0.3% by weight, based on the total weight of the thermographic composition;
            a second dye comprising (1-methylamino)anthraquinone which is present in an amount of 0.04% to 0.05% by weight, based on the total weight of the thermographic composition, or 1-[[4-(phenylazo)phenyl]azo]-2-naphthalenol which is present in an amount of 0.03% to 0.05% by weight, based on the total weight of the thermographic composition; and
            an activator comprising bisphenol A and 2,2', 4'4'-tetrahydroxybenzophenone, each of which is present in an amount of 0.1% to 0.3% by weight, based on the total weight of the thermographic composition, and wherein the activator also comprises arachidic acid in an amount of 0.01% to 0.03% by weight, based on the total weight of the thermographic composition; and
        wherein the relative amounts of OCNB and OBNB determine a melting point of the thermographic composition, and wherein the linear array of spaced apart recesses are radially arranged with respect to the center of the platform, wherein the thermographic compositions in the recesses in any one linear array are identical and have the same melting point, and wherein the radial arrangement is in an order corresponding to sequentially increasing melting points of the thermographic compositions over a diagnostically relevant temperature range of about 88° F. to about 106.7° F., wherein a difference between respective melting points of the thermographic compositions in the recesses of adjacent linear arrays is in a range of 0.2° F. to 1.0° F.
        wherein the thermographic composition, when in a solid state, exhibits a first color and, when in a liquid state, exhibits a second color, distinct from the first color, each of the first and second colors being visible to the naked eye.

2. The device of claim 1, wherein the temperature sensing module covers less than all of the first surface of the platform.

3. The device of claim 1, wherein alternate linear arrays of recesses have different numbers of recesses.

4. The device of claim 3, wherein the number of recesses in the linear arrays alternates between 7 and 15 recesses.

5. The device of claim 3, wherein the number of recesses in the linear arrays alternates between 8 and 14 recesses.

6. The device of claim 1, wherein the activator comprises an organic acid having a $pK_a$ of about 4 to about 12.

7. The device of claim 6, wherein the organic acid is selected from the group consisting of phenol, bisphenol A, arachidic acid, pyrocathechol and 3-nitrophenol, and combinations of two or more thereof.

8. The device of claim 1, wherein the second dye is (1-methylamino)anthraquinone.

9. The device of claim 1, wherein the second dye is 1-[[4-(phenylazo)phenyl]azo]-2-naphthalenol.

10. The device of claim 1, further comprising
    a releasable cover layer, having a shape corresponding to the platform, provided over the device and releasably attached to the first surface of the platform by the adhesive at the periphery.

11. The device of claim 1 in combination with a second device and instructional materials for using the device, wherein the device and second device and instructional materials are packaged as a kit.

12. The device of claim 1 further comprising a readable data structure disposed on one of the first and second surfaces of the platform.

13. The device of claim 1, wherein the platform is shaped to define three lobe areas.

14. The device of claim 1, wherein the plurality of linear arrays of recesses comprises 18 linear arrays of recesses.

15. A method for comparatively detecting temperature differentials in the same regions of a biological anatomy comprises:
    A) obtaining plural similar thermographic temperature sensing devices, each device having a temperature sensing module comprising:
        a heat conducting substrate comprising metallic foil, the substrate having a top surface and a plurality of linear arrays comprising a plurality of spaced apart recesses defined in the top surface;
        a protective layer of material disposed on the top surface of the heat conducting substrate;
        a thermographic composition disposed in each recess the thermographic composition comprising:
            a binary solvent system comprising relative amounts of ortho-chloronitrobenzene (OCNB) and ortho-bromonitrobenzene (OBNB);
            a first dye comprising crystal violet lactone which is present in an amount of 0.1% to 0.3% by weight, based on the total weight of the thermographic composition;

a second dye comprising (1-methylamino)anthraquinone which is present in an amount of 0.04% to 0.05% by weight, based on the total weight of the thermographic composition, or 1-[[4-(phenylazo)phenyl]azo]-2-naphthalenol which is present in an amount of 0.03% to 0.05% by weight, based on the total weight of the thermographic composition; and an activator comprising bisphenol A and 2,2', 4'4'-tetrahydroxybenzophenone, each of which is present in an amount of 0.1% to 0.3% by weight, based on the total weight of the thermographic composition, and wherein the activator also comprises arachidic acid in an amount of 0.01% to 0.03% by weight, based on the total weight of the thermographic composition;

wherein the relative amounts of OCNB and OBNB determine a melting point of the thermographic composition, and wherein the thermographic composition, when in a solid state, exhibits a first color and, when in a liquid state, exhibits a second color, distinct from the first color, each of the first and second colors being visible to the naked eye;

B) simultaneously applying each thermographic temperature sensing devices to one of symmetrically similar regions of the biological anatomy for a time duration; and C) comparing by visual inspection of the thermographic temperature sensing devices after the time duration of whether a difference in color of the recesses of the plurality of linear arrays exists between two of the sensing devices indicating a temperature differential between symmetrically similar regions of the biological anatomy.

16. The method of claim 15, wherein the thermographic compositions in the recesses in any one linear array are identical and have a same melting point within a diagnostically relevant temperature range.

17. The method of claim 15, wherein no two linear arrays contain thermographic compositions with the same melting point.

18. The method of claim 15, wherein the linear arrays are arranged in an order corresponding to sequentially increasing thermographic composition melting points.

19. The method of claim 15, wherein the different thermographic composition melting points in the plurality of linear arrays define the diagnostically relevant temperature range.

\* \* \* \* \*